US008778341B2

(12) United States Patent
Diaz et al.

(10) Patent No.: US 8,778,341 B2
(45) Date of Patent: Jul. 15, 2014

(54) ANTI-CK8 ANTIBODIES TO BE USED FOR TREATING COLORECTAL CANCERS AND IDENTIFYING METASTATIC AND/OR INVASIVE PHENOTYPES

(75) Inventors: Jean-Jacques Diaz, Venissieux (FR); Jean-Xavier Roca-Martinez, Lyons (FR); Jean-Christophe Saurin, Lyons (FR); Serge Petit, Villeurbanne (FR)

(73) Assignees: Universite Claude Bernard Lyon 1 (FR); Hospices Civils de Lyon (FR); Centre National de la Recherche Scientifique (FR)

( * ) Notice: Subject to any disclaimer, the term of this patent is extended or adjusted under 35 U.S.C. 154(b) by 230 days.

(21) Appl. No.: 13/322,255

(22) PCT Filed: May 27, 2010

(86) PCT No.: PCT/EP2010/057345
§ 371 (c)(1),
(2), (4) Date: Nov. 23, 2011

(87) PCT Pub. No.: WO2010/136536
PCT Pub. Date: Dec. 2, 2010

(65) Prior Publication Data
US 2012/0128681 A1 May 24, 2012

(30) Foreign Application Priority Data
May 27, 2009 (FR) ..................................... 09 53510

(51) Int. Cl.
*A61K 39/395* (2006.01)

(52) U.S. Cl.
USPC ..................................... 424/138.1; 424/139.1

(58) Field of Classification Search
None
See application file for complete search history.

(56) References Cited

U.S. PATENT DOCUMENTS

| 7,425,623 B2 * | 9/2008 | Brodin et al. .............. 530/388.8 |
| 2003/0138425 A1 * | 7/2003 | Mather ...................... 424/146.1 |

FOREIGN PATENT DOCUMENTS

| EP | 2034020 A1 | 3/2009 |
| WO | 03/057168 A2 | 7/2003 |
| WO | 2010/136536 | * 12/2010 |

OTHER PUBLICATIONS

Johansson et al Cacner Research vol. 59 p. 48 (1999).*
French Search Report relating to corresponding FR Application No. 0953510, issued Dec. 1, 2009.
International Search Report relating to corresponding PCT/EP2010/057345, issued Aug. 24, 2010.
English Translation of International Preliminary Report on Patentability relating to corresponding PCT/EP2010/057345, issued Dec. 9, 2011.
Doljak, et al., "Monoclonal Antibody to Cytokeratin VKIALEVEIATY Sequence Motif Reduces Plasminogen Activation in Breast Tumour Cells," Cancer Letters, 267 (2008) 75-84.
Erlandsson, et al., "Studies of the Interactions Between the Anticytokeratin 8 Monoclonal antibody TS1, its Antigen and its Anti-Idiotypic Antibody αTS1," Journal of Molecular Recognition, 2003, 16: 157-163.
Forest, et al., "Mise au point d'un modèle d'étude des effets d'une cryothérapie sur des tumeurs pulmonaires," Pathologie Biologie, 53 (2005) 199-203.
Gires, et al., "Cytokeratin 8 Associates with the External Leaflet of Plasma Membranes in Tumour Cells," Biochemical and Biophysical Research Communications, 328 (2005) 1154-1162.
Godfroid, et al., "Cytokeratins are Exposed on the Outer Surface of Established Human Mammary Carcinoma Cells," Journal of Cell Science, 99, 595-607 (1991).
Hembrough, et al., "A Cytokeratin 8-Like Protein with Plasminogen-Binding Activity is Present on the External Surfaces of Hepatocytes, HepG2 Cells and Breast Carcinoma Cell Lines," Journal of Cell Science, 108, 1071-1082 (1995).
Norrlund, et al., "Experimental Radioimmunotargeting Combining Nonlabeled, Iodine-125-Labeled, and Anti-Idiotypic Anticytokeratin Monoclonal Antibodies," Cancer, 1997, 80:2689-98.
Upasani, et al., "Database on Monoclonal Antibodies to Cytokeratins," Oral Oncology (2004) 40, 236-256.
Van Muijen, et al., Coexpression of Intermediate Filament Polypeptides in Human Fetal and Adult Tissues, Laboratory Investigation, vol. 57, No. 4, 359, 1987.
Waseem, et al., "Conformational Changes in the Rod Domain of Human Keratin 8 Following Heterotypic Association with Keratin 8 and Its Implication for Filament Stability," Biochemistry, 2004, 43, 1283-1295.
Weiner, et al., "Monoclonal Antibody Mechanisms of Action in Cancer," Immunol. Res. (2007) 39:271-278.

* cited by examiner

*Primary Examiner* — Sheela J Huff
(74) *Attorney, Agent, or Firm* — Banner & Witcoff, Ltd.

(57) ABSTRACT

The invention relates to antibodies specific to human CK8 and to pharmaceutical compositions for preventing and treating colorectal cancers. The invention also relates to methods for identifying colorectal cancers with an invasive and/or metastatic phenotype including detecting the cleavage of the C-terminal portion of human CK8 on the surface of tumor cells.

9 Claims, 7 Drawing Sheets

Figure 1:
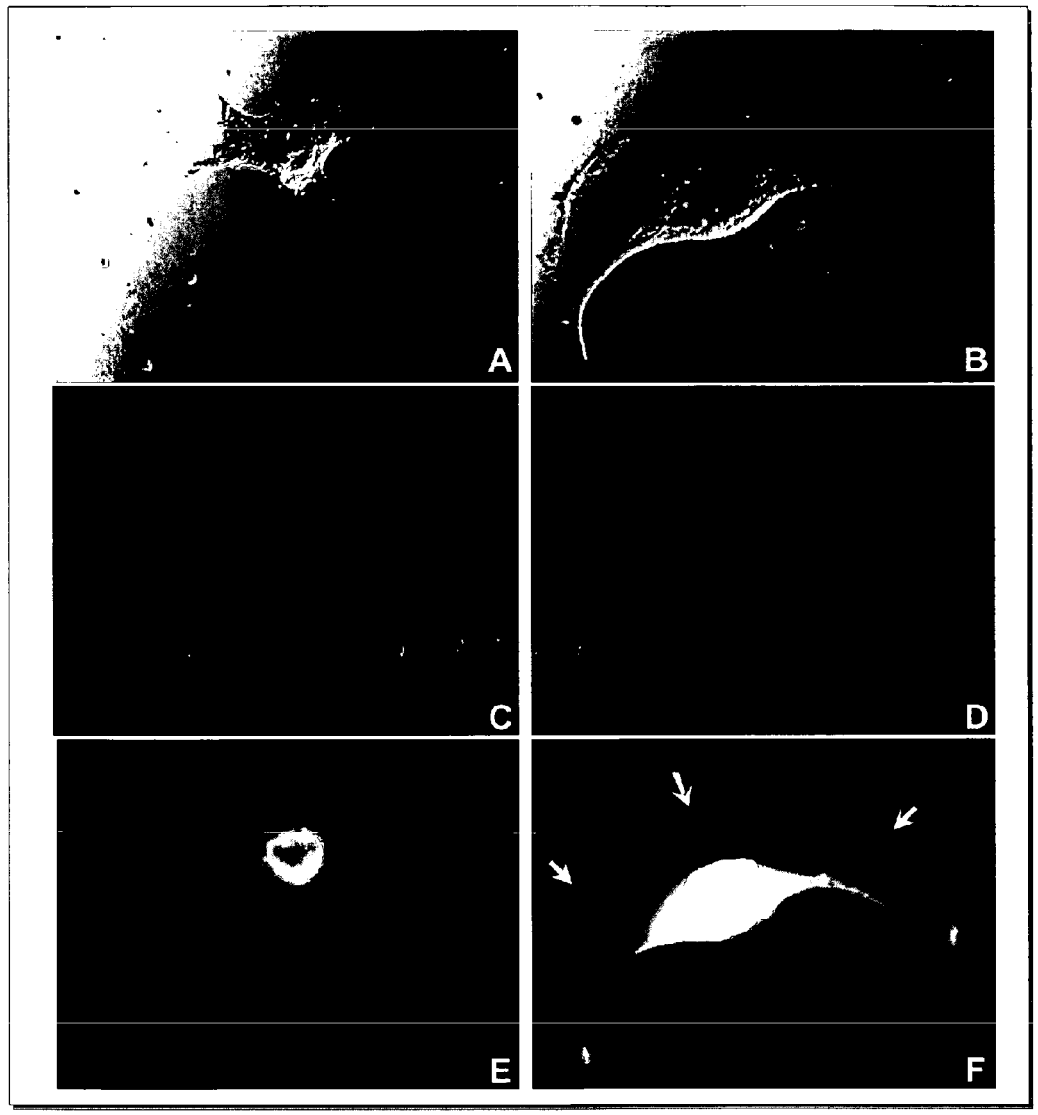

A.

B.

SEQUENCE LISTING

<160> NUMBER OF SEQ ID NOS: 3

<210> SEQ ID NO 1
<211> LENGTH: 483
<212> TYPE: PRT
<213> ORGANISM: Homo sapiens

<400> SEQUENCE: 1

```
Met Ser Ile Arg Val Thr Gln Lys Ser Tyr Lys Val Ser Thr Ser Gly
 1               5                  10                  15

Pro Arg Ala Phe Ser Ser Arg Ser Tyr Thr Ser Gly Pro Gly Ser Arg
            20                  25                  30

Ile Ser Ser Ser Phe Ser Arg Val Gly Ser Ser Asn Phe Arg Gly Gly
        35                  40                  45

Gly Leu Gly Gly Gly Tyr Gly Gly Ala Ser Gly Met Gly Gly Ile Thr
    50                  55                  60

Ala Val Thr Val Asn Gln Ser Leu Leu Ser Pro Leu Val Leu Glu Val
65                  70                  75                  80

Asp Pro Asn Ile Gln Ala Val Arg Thr Gln Glu Lys Glu Gln Ile Lys
                85                  90                  95

Thr Leu Asn Asn Lys Phe Ala Ser Phe Ile Asp Lys Val Arg Phe Leu
            100                 105                 110

Glu Gln Gln Asn Lys Met Leu Glu Thr Lys Trp Ser Leu Leu Gln Gln
        115                 120                 125

Gln Lys Thr Ala Arg Ser Asn Met Asp Asn Met Phe Glu Ser Tyr Ile
    130                 135                 140

Asn Asn Leu Arg Arg Gln Leu Glu Thr Leu Gly Gln Glu Lys Leu Lys
145                 150                 155                 160

Leu Glu Ala Glu Leu Gly Asn Met Gln Gly Leu Val Glu Asp Phe Lys
                165                 170                 175

Asn Lys Tyr Glu Asp Glu Ile Asn Lys Arg Thr Glu Met Glu Asn Glu
            180                 185                 190

Phe Val Leu Ile Lys Lys Asp Val Asp Glu Ala Tyr Met Asn Lys Val
        195                 200                 205

Glu Leu Glu Ser Arg Leu Glu Gly Leu Thr Asp Glu Ile Asn Phe Leu
    210                 215                 220

Arg Gln Leu Tyr Glu Glu Ile Arg Glu Leu Gln Ser Gln Ile Ser
225                 230                 235                 240

Asp Thr Ser Val Val Leu Ser Met Asp Asn Ser Arg Ser Leu Asp Met
                245                 250                 255

Asp Ser Ile Ile Ala Glu Val Lys Ala Gln Tyr Glu Asp Ile Ala Asn
            260                 265                 270

Arg Ser Arg Ala Glu Ala Glu Ser Met Tyr Gln Ile Lys Tyr Glu Glu
        275                 280                 285

Leu Gln Ser Leu Ala Gly Lys His Gly Asp Asp Leu Arg Arg Thr Lys
    290                 295                 300

Thr Glu Ile Ser Glu Met Asn Arg Asn Ile Ser Arg Leu Gln Ala Glu
305                 310                 315                 320

Ile Glu Gly Leu Lys Gly Gln Arg Ala Ser Leu Glu Ala Ala Ile Ala
                325                 330                 335

Asp Ala Glu Gln Arg Gly Glu Leu Ala Ile Lys Asp Ala Asn Ala Lys
            340                 345                 350

Leu Ser Glu Leu Glu Ala Ala Leu Gln Arg Ala Lys Gln Asp Met Ala
        355                 360                 365
```

```
Arg Gln Leu Arg Glu Tyr Gln Glu Leu Met Asn Val Lys Leu Ala Leu
    370             375             380
Asp Ile Glu Ile Ala Thr Tyr Arg Lys Leu Leu Glu Gly Glu Glu Ser
385             390             395             400
Arg Leu Glu Ser Gly Met Gln Asn Met Ser Ile His Thr Lys Thr Thr
            405             410             415
Ser Gly Tyr Ala Gly Gly Leu Ser Ser Ala Tyr Gly Gly Leu Thr Ser
            420             425             430
Pro Gly Leu Ser Tyr Ser Leu Gly Ser Ser Phe Gly Ser Gly Ala Gly
            435             440             445
Ser Ser Ser Phe Ser Arg Thr Ser Ser Ser Arg Ala Val Val Val Lys
            450             455             460
Lys Ile Glu Thr Arg Asp Gly Lys Leu Val Ser Glu Ser Ser Asp Val
465             470             475             480
Leu Pro Lys

<210> SEQ ID NO 2
<211> LENGTH: 30
<212> TYPE: PRT
<213> ORGANISM: Homo sapiens

<400> SEQUENCE: 2

Ala Glu Gln Arg Gly Glu Leu Ala Ile Lys Asp Ala Asn Ala Lys Leu
1               5                   10                  15
Ser Glu Leu Glu Ala Ala Leu Gln Arg Ala Lys Gln Asp Met
            20                  25                  30

<210> SEQ ID NO 3
<211> LENGTH: 12
<212> TYPE: PRT
<213> ORGANISM: Artificial
<220> FEATURE:
<223> OTHER INFORMATION: monoclonal antibody binding motif

<400> SEQUENCE: 3

Val Lys Ile Ala Leu Glu Val Glu Ile Ala Thr Tyr
1               5                   10
```

ANTI-CK8 ANTIBODIES TO BE USED FOR TREATING COLORECTAL CANCERS AND IDENTIFYING METASTATIC AND/OR INVASIVE PHENOTYPES

RELATED APPLICATION DATA

This application is a National Stage Application under 35 U.S.C. 371 of co-pending PCT application PCT/EP2010/057345 designating the United States and filed May 27, 2010; which claims the benefit of FR patent application number 0953510 and filed May 27, 2009 each of which are hereby incorporated by reference in their entireties.

The present invention concerns antibodies directed against cytokeratin 8 for the treatment of colorectal cancers. The invention also relates to polypeptide fragments derived from cytokeratin 8 and pharmaceutical and vaccine compositions for preventing and treating colorectal cancers.

Cytokeratin 8 (CK8) has been described as a protein belonging to the class of intermediate filaments, components of the cytoskeleton of epithelial cells. The structural function of intermediate filaments has been the subject of numerous studies.

Waseem et al. (Biochemistry, 43:1283-1295, 2004) studied the association of CK8 with CK18 and its involvement in the stability of cytokeratin filaments. This publication particularly describes various antibodies binding cytokeratins and in particular CK8, particularly including a monoclonal antibody M20 specifically binding to CK8.

More recently, proteins of the cytokeratin family have been described on the surface of carcinoma cells. Cytokeratin 8 would thus be present on the membrane of various cancer cells. Godfroid et al. (Journal of Cell Science, 99: 595-607) have described the presence of cytokeratins 8, 18 and 19 on the surface of cultured breast carcinoma cells. Hembrough et al. (Journal of Cell Science, 108:1071-1082, 1995) have described the presence of CK8 or a "CK8 like" protein on the surface of hepatocytes, HepG2 cells and breast carcinoma cells. Cytokeratin 8 has also been detected on the surface of carcinomas of other cancers such as upper digestive tract cancer (Gires et al., Biochemical and Biophysical Research Communications, 328:1154-1162, 2005).

Erlandsson et al. (J. of Molecular Recognition, 16:157-163, 2003) describe the monoclonal antibody TS1 directed against human CK8 and its anti-idiotype αTS1 as well as their use in immunotherapy for the treatment of carcinomas. According to this document, antibody TS1 has proven effective in the nude mouse model for hepatocarcinoma.

International Application W003/057168 discloses the presence of new epitopes on the surface of colon, breast, ovary, kidney, lung and testicle cancer tumor cells. These new epitopes are not detected in healthy cells and would be derived from human cytokeratins 8 and 18 (CK8 and CK18). According to application W003/057168, these cytokeratins are cleaved in their N-terminal part in tumor cells and form a complex on the surface of cells exposing new epitopes specific for cancer cells. However, all these new epitopes combine sequences of CK8 and CK18.

The membrane role of CK8 has been studied and the results obtained suggest that CK8 is involved in mechanisms of degradation of the extracellular matrix (ECM). CK8 would have the role of a plasminogen receptor at the surface of tumor cells. CK8 participates in the formation of a protein complex for cleaving plasminogen to plasmin. Plasmin is the enzyme that degrades the proteins of the extracellular matrix.

Doljak et al. (Cancer Letters, 267:75-84, 2008) have described a monoclonal antibody binding the motif VKIA-LEVEIATY (SEQ ID NO:3) conserved in different cytokeratins. This monoclonal antibody notably binds CK2, CK8, CK10 and CK18 in MCF-7 breast cancer cells. These antibodies inhibit the activation of plasminogen on MCF-7 cells in vitro.

However, despite the identification of many antigens on the surface of tumor cells and the progress made in understanding the mechanisms involved, therapeutic needs remain significant, especially for treating cancers with high metastatic potential, limiting formation of metastases and limiting chemoresistance.

Moreover, metastases are observed either immediately or secondarily in 40-60% of cases of colorectal cancer. Predicting the risk of metastases is crucial for guiding the therapy of patients with colorectal cancer, particularly in deciding to treat the patient preventatively before the appearance of metastases (adjuvant to surgery). Adjuvant chemotherapy is not recommended in stage T3N0 and yet nearly 30% of patients in this category will develop metastases. Methods allowing identifying a colorectal cancer having an invasive or metastatic phenotype would therefore be very useful for determining the appropriate treatment for patients.

The present invention has now discovered that antibodies directed specifically against CK8 and in particular against certain fragments of CK8 have an inhibitor effect on the invasive capacity and growth of colorectal cancer tumor cells in in vitro and in vivo tests. In particular, the invention concerns the use of these antibodies for the treatment of invasive colorectal cancers. These antibodies are therefore especially useful for the prevention and treatment of metastases in colorectal cancers.

In fact, it has now been demonstrated that the invasive capacity of colon adenocarcinoma tumor cells induced by bombesin is accompanied by cleavage of the C-terminal part of human CK-8. The cleaved form of human CK8 is detected at the tumor cell membrane. This cleaved CK8 is then located at the surface of invadopodia-type membrane structures characteristic of the invasive forms of tumor cells.

Remarkably, a monoclonal antibody specifically binding human CK8, called M20, inhibits the invasive capacity of these tumor cells after induction by bombesin. This antibody recognizes and specifically binds the uncleaved part of human CK8 present on the surface of colon adenocarcinoma tumor cells. In contrast, antibody 1E8, recognizing the cleaved part of human CK8, did not have an effect on invasive tumor cells treated with bombesin.

Furthermore, these in vitro results obtained in tumor cells treated with bombesin could be confirmed by in vivo tests in nude mice after subcutaneous injection of ISRECO-1 tumor cells. In these mice, monoclonal antibody M20 clearly inhibits tumor growth.

While many antigens, and especially various cytokeratins, have been described on the surface of tumor cells, it is shown for the first time that antibodies directed specifically against a region of human CK8 have an inhibitor effect in vivo on the growth of colorectal adenocarcinoma tumor cells. Moreover, the present invention shows that to obtain a therapeutic effect, antibodies binding human CK8 must bind to specific regions of this CK8, particularly the uncleaved part of the molecule. Polypeptide fragments of CK8 specifically recognized by antibody M20 have thus been identified.

These results open up completely novel therapeutic prospects for treating colorectal cancers, and more particularly treating invasive colorectal cancers, based on antibodies specifically binding certain fragments of human CK8 and, in particular, binding the fragment of CK8 recognized by monoclonal antibody M20.

Figure 2:
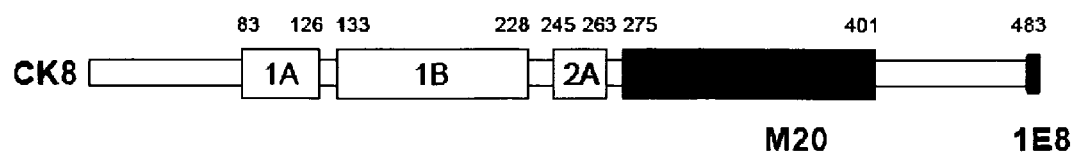
Figure 2:
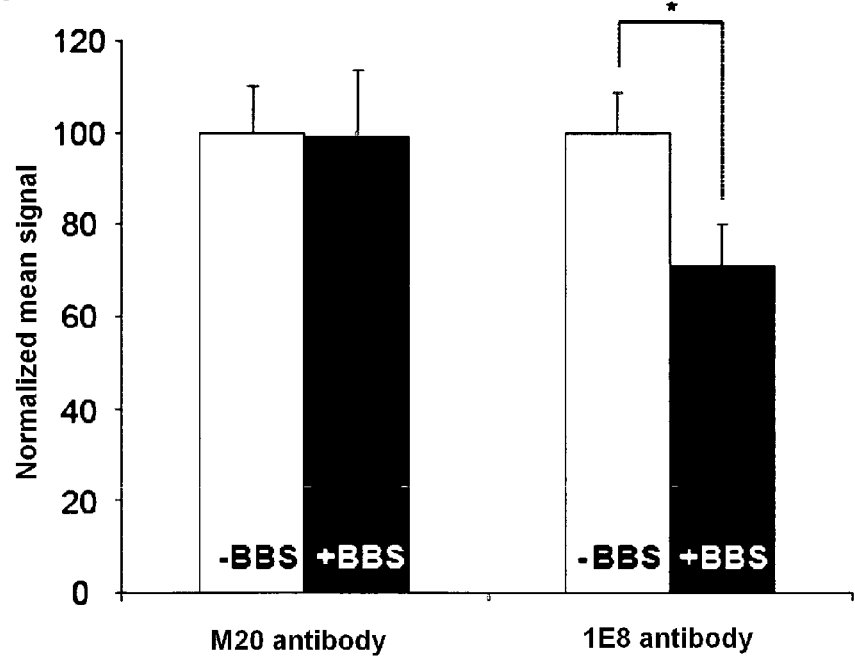

The results obtained show that CK8 is exposed on the surface of not yet invasive colorectal cancer cells. CK8 undergoes a cleavage in its C-terminal part when the cell is stimulated by a gastric peptide that renders the cell invasive. The C-terminal fragment is then released while the N-terminal part of CK8 remains exposed on the surface of invasive colorectal cancer cells (FIG. 2).

Detecting the cleavage of CK8 on the surface of colorectal cancer cells therefore permits identifying invasive or metastatic cells and consequently adjusting the treatment.

SUMMARY OF THE INVENTION

The invention relates to antibodies or antibody fragments, specifically binding the polypeptide derived from human CK8 with the sequence corresponding to the amino acids of position 1 to position 401 of SEQ ID No. 1 for use for treating colorectal cancers.

Preferably, the antibodies or antibody fragments specifically bind the polypeptide derived from human CK8 with the sequence corresponding to the amino acids of position 275 to position 401 of SEQ ID No. 1 and more preferentially, the antibodies or antibody fragments specifically bind the polypeptide derived from human CK8 with the sequence corresponding to the amino acids of position 338 to position 367 of SEQ ID No. 1.

In the embodiments, the antibodies or antibody fragments specifically bind a fragment of at least 10 amino acids of the polypeptide derived from human CK8 with the sequence corresponding to the amino acids of position 338 to position 367 of SEQ ID No. 1.

Advantageously, the antibodies or antibody fragments according to the invention are used for preventing or treating invasive and/or metastatic colorectal cancers.

The invention also relates to pharmaceutical compositions containing an antibody according to the invention and an appropriate pharmaceutical carrier, for use for treating colorectal cancers.

Another subject of the invention is a method for identifying a colorectal cancer with an invasive and/or metastatic phenotype consisting of the following steps:
  Detecting the cleavage of the C-terminal part of CK8 in a sample previously taken from a patient,
  Classifying the colorectal cancer as invasive and/or metastatic when the C-terminal part of CK8 is cleaved.

Preferably, the cleavage of the C-terminal part of CK8 is detected in a sample of colorectal cancer cells previously taken from a patient.

Preferably, detecting the cleavage of the C-terminal part of CK8 consists of detecting the total or partial loss of the C-terminal part of human CK8 by means of an antibody specifically binding a polypeptide derived from human CK8 with the sequence corresponding to the amino acids of position 402 to position 483 of SEQ ID No. 1.

Preferably, detecting the cleavage of the C-terminal part of CK8 also consists of detecting the N-terminal part of human CK8 by means of an antibody specifically binding a polypeptide derived from human CK8 with the sequence corresponding to the amino acids of position 1 to position 401 of SEQ ID No. 1.

In the methods according to the invention, the cleavage of the C-terminal part of CK8 in a sample previously taken from a patient is detected by immunohistochemistry or immunofluorescence.

In preferred embodiments, the cleavage of the C-terminal part of CK8 is detected in a blood sample previously taken from a patient and in which blood sample the C-terminal part of human CK8 is detected by means of an antibody specifically binding a polypeptide derived from human CK8 with the sequence corresponding to the amino acids of position 402 to position 483 of SEQ ID No. 1.

The invention also relates to a diagnostic kit for identifying colorectal cancer with an invasive and/or metastatic phenotype comprising an antibody specifically binding a polypeptide derived from human CK8 with the sequence corresponding to the amino acids of position 402 to position 483 of SEQ ID No. 1 and an antibody specifically binding a polypeptide derived from human CK8 with the sequence corresponding to the amino acids from position 1 to position 401 of SEQ ID No. 1.

Preferably, the methods according to the invention for identifying a colorectal cancer with an invasive and/or metastatic phenotype are in vitro methods.

SEQUENCE LISTING

SEQ ID No. 1: Amino acid sequence of human cytokeratin 8 (Genbank P05787)
SEQ ID No. 2: Amino acid sequence of a peptide derived from human cytokeratin corresponding to amino acids A338 to M367.

DESCRIPTION OF THE INVENTION

The invention relates to the use of antibodies specific for the N-terminal or C-terminal regions of human CK8 for therapeutic and diagnostic purposes. The invention relies on the observation that in colorectal cancer cells, the appearance of invasive and/or metastatic cells is accompanied by a cleavage of human CK8 exposed on the surface of these cells. The N-terminal part of CK8 remains exposed on the surface of colon adenocarcinoma cells while the C-terminal part of the protein disappears partially or completely from the surface of these cells. Antibodies specific for the N-terminal part of human CK8 inhibit tumor growth, the development of invasive cells and the development of metastases in vitro and in vivo. The appearance of the cleaved form of human CK8 on the surface of colon adenocarcinoma cells is a marker of invasive and/or metastatic phenotypes.

The antibodies used in the present invention bind or attach to the selected fragments of CK8. Preferably, these antibodies specifically bind chosen fragments of human CK8.

"Specifically bind" means that these antibodies bind only to CK8 and preferably only to human CK8. In particular, the antibodies do not bind to other antigens and especially not to other human cytokeratins such as CK1, CK2, CK10 and CK18.

The antibodies according to the present invention are preferably specific monoclonal antibodies, particularly murine, chimeric or humanized, which may be obtained according to the standard methods well known to the person skilled in the art.

In general, for preparing monoclonal antibodies or their functional fragments, particularly of murine origin, one can refer to the techniques that are described in the manual Antibodies (Harlow and Lane, Antibodies: A Laboratory Manual, Cold Spring Harbor Laboratory, Cold Spring Harbor N.Y., pp. 726, 1988) or to the hybridoma preparation technique well known to the person skilled in the art.

The monoclonal antibodies according to the invention may be obtained, for example, from cells of an animal immunized with a fragment of CK8, in particular with the peptide of SEQ ID No. 2, with a peptide having the epitope recognized specifically by monoclonal antibody M20 or with the C-terminal part of human CK8. Said fragments of human CK8 could be produced according to the usual operating procedures for expression in a recombinant host organism or by peptide synthesis, for example.

The monoclonal antibodies according to the invention could be purified, for example, on an affinity column on which has been previously immobilized a fragment of human CK8, the peptide of SEQ ID No. 2, another peptide containing the epitope specifically recognized by monoclonal antibody M20 or a fragment derived from the C-terminal part of human CK8. Other purification techniques well known to the person skilled in the art could be used simultaneously or successively.

Antibody means both chimeric and humanized antibodies.

Chimeric antibody means an antibody that contains a natural variable region (light chain and heavy chain) derived from an antibody from a given species in combination with the constant regions of the light chain and heavy chain of an antibody of a species heterologous to said given species.

Antibodies or their chimeric fragments according to the invention can be prepared by using genetic recombination techniques. For example, chimeric antibodies can be made by cloning recombinant DNA bearing a promoter and a sequence coding for the variable region of a non-human, particularly murine, monoclonal antibody, such as monoclonal antibody M20, and a sequence coding for the constant region of a human antibody. A chimeric antibody of the invention encoded by such a recombinant gene will be a mouse-human chimera, for example, the specificity of this antibody being determined by the variable region derived from murine DNA and its isotype determined by the constant region derived from human DNA. Methods for preparing chimeric antibodies are fully described in the literature.

Humanized antibody means an antibody that contains CDRs derived from an antibody of non-human origin, the other parts of the antibody molecule being derived from one (or more) human antibodies. Moreover, some skeleton segment residues (called FR) can be modified to conserve the binding affinity.

Humanized antibodies or their fragments can be prepared by techniques known to the person skilled in the art. Such humanized antibodies are preferred for the therapeutic uses of the present invention.

The invention also relates to the use of antibody fragments specifically binding to a chosen fragment of human CK8 for the treatment of colorectal cancers or for diagnosis of invasive or metastatic forms of colorectal cancer. Typically, these antibody fragments are functional, so they conserve their ability to bind or attach to human CK8 fragments, and notably to the peptide of SEQ ID No. 2 derived from CK8 or the C-terminal part of human CK8.

Antibody fragment according to the invention particularly designates an antibody fragment, such as Fv, scFv (sc for single chain) Fab, F(ab')2, Fab', scFv-Fc fragments or diabodies, or any fragment whose half-life was increased by chemical modification. Generally, this fragment can exert a partial same activity of the antibody from which it comes, such as, in particular, the ability to recognize and bind fragments of CK8. In one advantageous embodiment, this antibody fragment is able to inhibit the invasiveness and growth of tumor cells.

Preferably, said functional fragments would be made up of or comprise a partial sequence of the variable heavy or light chain of the antibody from which they are derived, said partial sequence being sufficient to retain the same binding specificity as the antibody from which it comes and a sufficient affinity, preferably at least equal to $1/100$, more preferably equal to at least $1/10$ of that of the antibody from which it comes, with regard to human CK8.

Such a functional fragment would comprise at least 5 amino acids, preferably 10, 15, 25, 50 and 100 consecutive amino acids of the antibody sequence from which it comes.

Preferably, these functional fragments will be Fv, scFv, Fab, F(ab')2, F(ab'), scFv-Fc fragments or diabodies, which generally have the same binding specificity as the antibodies from which they come. According to the present invention, the antibody fragments of the invention can be obtained from antibodies such as previously described by methods including digestion by enzymes like pepsin or papain and/or by cleavage of the disulfide bridges by chemical reduction. Alternatively, the antibody fragments comprised in the present invention can be obtained by genetic recombination techniques also well known to the person skilled in the art or even by peptide synthesis.

A first subject of the invention is an antibody or antibody fragment used for treating colorectal cancers, specifically binding the polypeptide derived from human CK8 with the sequence corresponding to the amino acids of position 1 to position 367, 380, 393 or 401 of SEQ ID No. 1.

The invention also concerns an antibody or antibody fragment used for treating colorectal cancers, specifically binding the polypeptide derived from human CK8 with the sequence corresponding to the amino acids of position 275 to position 367, 380, 393 or 401 of SEQ ID No. 1.

The invention also concerns an antibody or antibody fragment used for treating colorectal cancers, specifically binding the polypeptide derived from human CK8 with the sequence corresponding to the amino acids of position 338 to position 367, 380, 393 or 401 of SEQ ID No. 1.

More preferentially, the invention relates to an antibody or antibody fragment such as described above for use for preventing or treating invasive and/or metastatic colorectal cancers.

More preferentially, the invention relates to an antibody or antibody fragment such as described above for use for preventing or treating metastatic tumors or metastases in colorectal cancer.

Another subject of the invention is a method for identifying a colorectal cancer with an invasive and/or metastatic phenotype consisting of the following steps:
Detecting the cleavage of the C-terminal part of CK8 in a sample previously taken from a patient,
Classifying the colorectal cancer as invasive and/or metastatic when the C-terminal part of CK8 is cleaved.

As cytoskeleton proteins, cytokeratins are not usually exposed on the surface of healthy cells. It was known that in certain cancers, epitopes derived from cytokeratins can be detected on the surface of tumor cells. It has now been found that human CK8 is exposed on the surface of tumor cells in colorectal cancer. Furthermore, the invasive capacity of colon adenocarcinoma tumor cells is characterized by the cleavage of the C-terminal part of human CK8. Only the N-terminal part of CK8 remains on the surface of these tumor cells. The cleavage site is located near the C-terminal end of domain 2B of human cytokeratin (domain corresponding to positions 275-401 in SEQ ID No. 1).

More precisely, the cleavage site could be located at position 393 of human cytokeratin of SEQ ID No. 1.

The term "N-terminal part of human CK8" refers to the polypeptide of position 1 to position 401 of human CK8 of SEQ ID No. 1 and preferably to the polypeptide of position 1 to position 393 of human CK8.

The term "C-terminal part of human CK8" refers to the polypeptide of position 402 to position 483 of human CK8 of SEQ ID No. 1 and preferably to the polypeptide of position 402, 410, 420, 430, 440 or 450 to position 483 of human CK8 of SEQ ID NO. 1.

Only antibodies directed against the N-terminal part of human CK8 have an inhibitor effect in vitro and in vivo on tumor growth and more particularly the antibodies specifically binding the polypeptides derived from human CK8 described above.

Antibodies directed against the C-terminal part, in contrast, do not have an inhibitor effect; these antibodies can be used for diagnostic purposes to detect the cleavage of human CK8 and thus identify colorectal cancers with an invasive and/or metastatic phenotype.

Preferably, the cleavage of the C-terminal part of CK8 is detected in a sample of colorectal cancer cells previously taken from a patient.

Sample, in the present invention, means tumor cells taken from a patient such as, for example, a biopsy from a tissue or organ affected by colorectal cancer.

Any appropriate method can be used to detect the cleavage of the C-terminal part of CK8. Preferably, this detection concerns detecting the loss of a C-terminal fragment of human CK8 corresponding to the polypeptide of position 402, 410, 420, 430, 440 or 450 to position 483 of human CK8 of SEQ ID NO. 1.

For example, cleavage can be detected by determining the molecular weight of the human CK8 present in the sample cells. Measuring the molecular weight can detect the loss of the C-terminal part of CK8. This operation may be done by western blot or by any other method by means of antibodies specific for the N-terminal part of human CK8.

Alternatively, the cleavage of the C-terminal part of human CK8 can be detected by measuring the total or partial loss of the C-terminal part of human CK8 on the surface of the tumor cells of the sample. Cleavage, and therefore the loss of the C-terminal part of CK8, can, for example, be detected by means of an antibody specific for the C-terminal part of human CK8, and more particularly an antibody specifically binding a polypeptide derived from CK8 corresponding to the polypeptide of position 402, 410, 420, 430, 440 or 450 to position 483 of human CK8 of SEQ ID NO. 1.

Preferably, detecting the cleavage of the C-terminal part of CK8 consists of detecting the total or partial loss of the C-terminal part of human CK8 by means of an antibody specifically binding a polypeptide derived from human CK8 with the sequence corresponding to the amino acids of position 402 to position 483 of SEQ ID No. 1.

Advantageously, the detection of the cleavage of CK8 is measured by means of two antibodies respectively binding the N-terminal part and the C-terminal part of human CK8. The signal differential obtained with the two antibodies allows measuring the partial or total loss of the C-terminal part of human CK8 on the surface of the sample tumor cells.

Preferably, detecting the cleavage of the C-terminal part of CK8 also comprises detecting the N-terminal part of human CK8 by means of an antibody specifically binding a polypeptide derived from human CK8 with the sequence corresponding to the amino acids of position 393 or 401 of SEQ ID No. 1.

In the methods according to the invention, the cleavage of the C-terminal part of CK8 in a sample previously taken from a patient is detected by immunohistochemistry or immunofluorescence.

In preferred embodiments, the cleavage of the C-terminal part of CK8 is detected in a blood sample previously taken from a patient and in which blood sample the C-terminal part of human CK8 is detected by means of an antibody specifically binding a polypeptide derived human CK8 with the sequence corresponding to the amino acids of position 402, 410, 420, 430, 440 or 450 to position 483 of human CK8 of SEQ ID No. 1.

The invention also relates to a diagnostic kit for identifying colorectal cancer with an invasive and/or metastatic phenotype comprising an antibody specifically binding a polypeptide derived from human CK8 with the sequence corresponding to the amino acids of position 402, 410, 420, 430, 440 or 450 to position 483 of SEQ ID No. 1 and an antibody specifically binding a polypeptide derived from human CK8 with the sequence corresponding to the amino acids from position 393 or position 401 of SEQ ID No. 1.

The invention also relates to a polypeptide chosen from the group consisting of:

a) a polypeptide derived from human CK8 with the sequence corresponding to amino acids of position 1 to position 401 of SEQ ID No. 1, b) a polypeptide derived from human CK8 with the sequence corresponding to amino acids of position 275 to position 401 of SEQ ID No. 1, c) a polypeptide derived from human CK8 with the sequence corresponding to amino acids of position 338 to position 367 of SEQ ID No. 1, d) a fragment of at least 10 amino acids of a polypeptide derived from human CK8 with the sequence corresponding to amino acids of position 338 to position 367 of SEQ ID No. 1, e) a polypeptide from human CK8 with the sequence corresponding to amino acids 402, 410, 420, 430, 440 or 450 to position 483 of SEQ ID No. 1.

The invention therefore relates to fragments of human CK8 corresponding to polypeptides with the sequence corresponding to amino acids of position 1 to position 367, 380, 393 or 401 of SEQ ID No. 1.

The invention also relates to fragments of human CK8 corresponding to polypeptides with the sequence corresponding to amino acids of position 275 to position 367, 380, 393 or 401 of SEQ ID No. 1.

The invention also relates to fragments of human CK8 corresponding to polypeptides with the sequence corresponding to amino acids of position 338 to position 367, 380, 393 or 401 of SEQ ID No. 1.

The invention also relates to fragments of these polypeptides comprising at least 5, 10, 15 or 20 amino acids.

Preferably, the invention concerns these polypeptides for use as a medicament.

Preferably, the invention concerns these polypeptides for the prevention and/or treatment of cancer.

More preferentially, the invention concerns these polypeptides for the prevention and/or treatment of colorectal cancers and in particular invasive or metastatic colorectal cancers.

The present invention therefore also relates to polypeptide fragments and peptides derived from human CK8. The invention also relates to modified peptides derived from CK8. Peptide modifications are well known to the person skilled in the art.

The invention also particularly concerns the peptide of SEQ ID No. 2. This peptide is recognized by antibody M20; it corresponds to positions 338 to 367 of human CK8 (Genbank P05787 K2C8 Human Keratin). M20 antibodies are specific for human cytokeratin 8 and inhibit the growth and invasiveness of tumor cells in in vitro and in vivo tests.

The invention also concerns fragments of at least 5, 7, 10, 15 or 20 amino acids of the peptide of SEQ ID No. 2. These peptide fragments preferentially comprise at least one epitope of the peptide according to SEQ ID No. 2. The present invention has shown that monoclonal antibody M20 specifically recognizes the peptide of SEQ ID No. 2 corresponding to positions 338 to 367 of human CK8. Preferably, the peptide fragments of SEQ ID No. 2 comprise the epitope (or antigenic determinant) recognized by monoclonal antibody M20 specifically binding human CK8.

Epitope means a molecule that can be recognized by a paratope (variable part of an antibody or T cell membrane receptor (TCR) to determine whether it belongs to a self domain or a non-self domain.

Monoclonal antibody M20 sold by Sigma® has been described by Van Muijen, G. et al. (Lab. Invest., 57: 359, 1987). The antigenic epitope specifically recognized by antibody M20 could be determined more precisely from the peptide of SEQ ID No. 2 according to techniques well known to the person skilled in the art. The person skilled in the art will also identify the other epitopes present in the peptide of SEQ ID No. 2 that can elicit an immune response able to inhibit the growth and invasiveness of tumor cells.

Preferably, the fragments of the peptide of SEQ ID No. 2 according to the present invention comprise the Lys-Leu (KL) sequence corresponding to positions 15-16 of SEQ ID No. 2. These amino acids correspond to two amino acids K352 and L353 of human CK8. The present invention has shown that the epitope of antibody M20 comprises these sequences.

The invention also relates to peptides with at least 90%, 95%, 98% and preferentially at least 99% of amino acids identical to the peptide of SEQ ID No. 2.

Identical amino acids means amino acids that are invariant or unchanged between two sequences. These polypeptides can have a deletion, an addition or a substitution of at least one amino acid with regard to the polypeptide of SEQ ID No. 2.

The invention also relates to peptides with at least 90%, 95%, 98% and preferentially at least 99% similarity to the peptide of SEQ ID No. 2.

Similarity means the measurement of the resemblance between protein sequences. These polypeptides can have a deletion, an addition or a substitution of at least one amino acid with regard to SEQ ID No. 2. The degree of similarity between two sequences, quantified by a score, is based on the percentage of conserved identities and/or substitutions of the sequences.

The methods for measuring and identifying the degree of identity and degree of similarity between polypeptides are known to the person skilled in the art. For example, Vector NTi 9.1.0, alignment program AlignX (Clustal W algorithm) (Invitrogen INFORMAX, at the World Wide Web site Invitrogen dot com) can be used. Preferably, the default parameters are used.

The invention also relates to polynucleotides coding for polypeptides, polypeptide fragments and peptides derived from human CK8 described above.

More preferentially, the invention relates to these polynucleotides for use as a medicament.

The invention also relates to the peptide of SEQ ID No. 2 and a polynucleotide coding for this peptide.

The invention also relates to polynucleotides coding for polypeptides and peptides such as defined above. Due to the degeneracy of the genetic code, different polynucleotides can code for a polypeptide or peptide, such as defined above.

According to the present invention, "polynucleotide" means a single stranded DNA or RNA nucleotide chain or its complement, or a double stranded cDNA (complementary DNA) or genomic DNA nucleotide chain. Preferably, the polynucleotides of the invention are DNA, particularly double stranded DNA. The term "polynucleotide" also designates modified polynucleotides.

The polynucleotides of the present invention are isolated or purified from their natural environment. Preferably, the polynucleotides of the present invention can be prepared by conventional molecular biology techniques such as described by Sambrook et al. (Molecular Cloning: A Laboratory Manual, 1989) or by chemical synthesis.

The invention also has for a subject a pharmaceutical composition comprising an antibody, a polypeptide, a polynucleotide and/or a peptide according to the invention.

The invention concerns pharmaceutical compositions comprising an antibody, a polypeptide, a peptide or a polynucleotide such as defined in the present invention and an appropriate pharmaceutical carrier.

These compositions can be formulated for administration to mammals, including humans. The dosage varies according to the treatment and according to the condition in question. These compositions are made so as to be administered by digestive or parenteral route.

In the pharmaceutical compositions of the present invention for oral, sublingual, subcutaneous, intramuscular, intravenous, transdermal, local or rectal administration, the active ingredient can be administered in the form of administration units, mixed with conventional pharmaceutical carriers, to animals or human beings. Appropriate administration unit forms include oral forms such as tablets, gel capsules, powders, granules and oral solutions or suspensions, sublingual and buccal administration forms, subcutaneous, intramuscular, intravenous, intranasal or intraocular administration forms and rectal administration forms.

When a solid composition is prepared in the form of tablets, the main active ingredient is mixed with a pharmaceutical carrier such as gelatin, starch, lactose, magnesium stearate, talc, gum arabic, or the like. The tablets can be coated with saccharose or other appropriate materials or even be treated so that they have an extended or delayed activity and that they continuously release a predetermined quantity of active ingredient.

A gel capsule preparation is obtained by mixing the active ingredient with a diluent and pouring the mixture obtained into hard or soft gel capsules.

A preparation in the form of a syrup or elixir can contain the active ingredient conjointly with a sweetener, an antiseptic and an appropriate taste enhancer and coloring agent.

Powders or granules dispersible in water can contain the active ingredient in mixture with dispersing or wetting agents or suspending agents, and with flavor enhancers or sweeteners.

The invention also concerns vaccine compositions comprising a polypeptide, a peptide and/or a polynucleotide, such as defined in the present invention and an appropriate adjuvant. In vaccination, adjuvants are conventionally defined as substances that can potentiate or modulate the immune response against one or more co-administered antigens. Vaccines are usually inoculated by injection, but they can be given orally or by nasal spray.

The invention relates to pharmaceutical or vaccine compositions for preventing and/or treating cancers.

The invention also concerns therapeutic methods for treating colorectal cancers consisting of administering to an individual an effective quantity of antibodies specifically binding the human CK8 fragments defined in the present invention and especially the fragment of SEQ ID No. 2. The invention also concerns therapeutic methods for treating cancers including administering to an individual an effective quantity of a polypeptide or polynucleotide derived from CK8 such as described in the present invention.

The invention finally concerns the use of antibodies, polypeptides and polynucleotides such as defined in the present invention for the production of cancer treatment drugs.

In one preferred embodiment, the present invention relates to compositions for preventing and/or treating cancer.

"Cancer" means all malignant neoplastic formations, regardless of their histological nature. There are two major categories of malignant tumors: carcinomas of epithelial origin, and sarcomas, of conjunctive origin. Malignant tumors are formed of atypical cells, invasive or spreading, characterized generally by an ability to grow autonomously, an imprecise delineation, an ability to invade neighboring tissues and vessels and a tendency to spread through the production of metastases.

Preferably, the compositions according to the invention prevent and/or treat colorectal cancers and, more particularly, invasive or metastatic cancers.

FIGURES

FIG. 1: Immunofluorescence analysis of cytokeratin 8 in cells modified by bombesin activation. Isreco 1 cells were plated on 12-mm glass slides previously coated with 1 ng/mL Matrigel. They were then treated for 1 h in a medium containing 10 nM bombesin. The slides were contacted with anti-cytokeratin 8 antibodies then with DAPI (nuclear marker). A, C and E show images of an untreated cell. B, D and F show images of a cell activated by bombesin. Photos A and B correspond to differential interference contrast. Photos C and D show the DAPI fluorescence. Photos E and F show the fluorescence corresponding to the anti-cytokeratin 8 antibody (M20). The yellow arrows show the presence of CK8 along the lamellipodium of the cell.

FIG. 2: Study by flow cytometry of the presence on the membrane of M20 and 1E8 epitopes of cytokeratin 8. Three Isreco 1 cell samples were studied by flow cytometry in four different experiments (FIG. 26). Each cell sample was divided into three fractions respectively labeled by anti-cytokeratin 8 antibodies M20 and 1E8, the third fraction being labeled only by the secondary antibody alone. Once the residual signal of the secondary antibody is subtracted, the anti-cytokeratin 8 antibody signals were averaged and normalized. A. Position of the epitopes of antibodies M20 and 1E8 on the cytokeratin 8 sequence. B. Graph of the normalized means of the signals of each antibody applied to bombesin-treated and untreated cells. Significance: $*=p<0.05$.

Figure 3A:
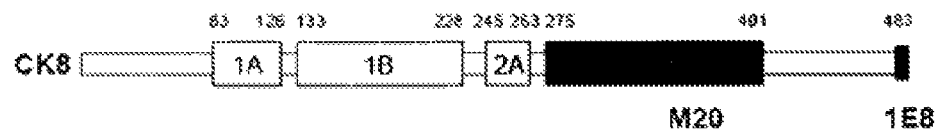
Figure 3A:
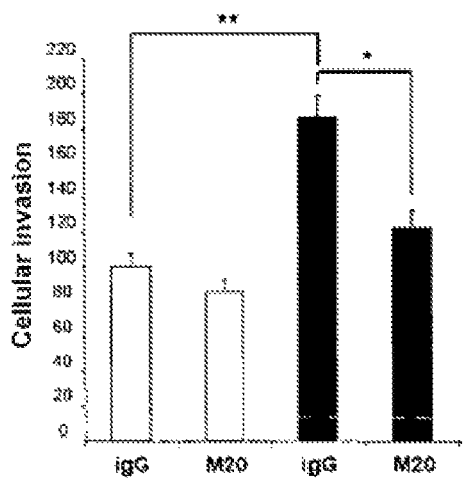
Figure 3A:
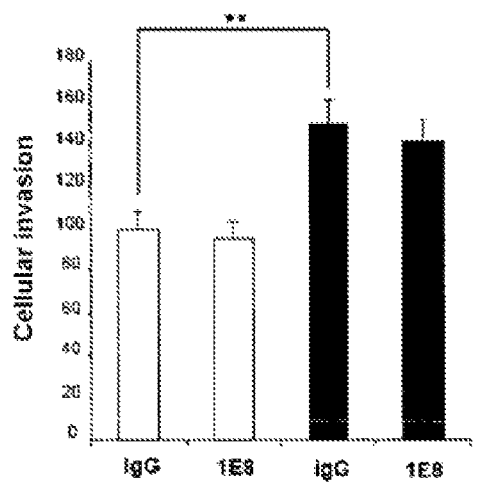
Figure 3B:
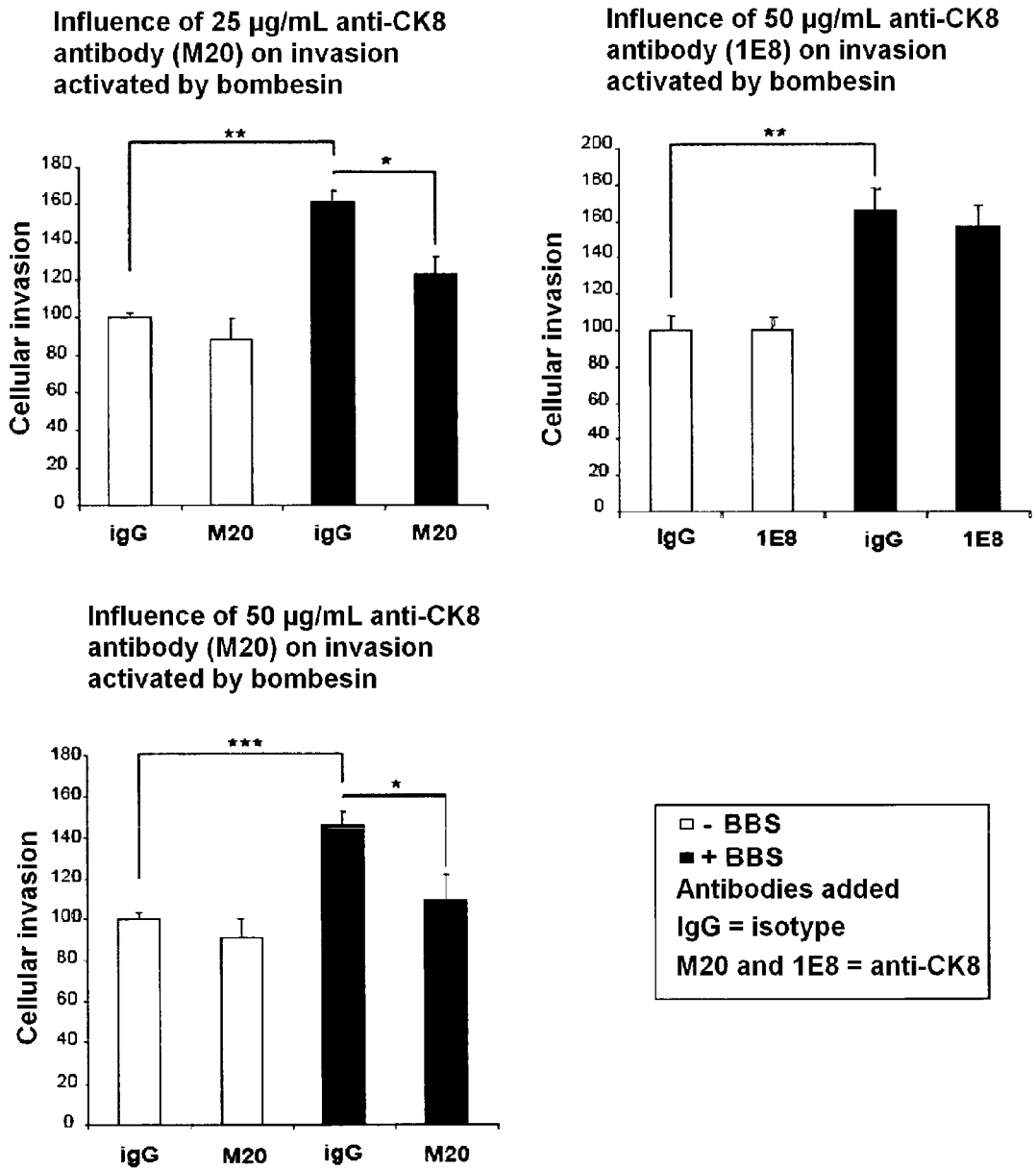

FIGS. 3A-3B: Study of the invasion of Isreco 1 cells induced by activation with bombesin in the presence of anti-cytokeratin 8 antibodies M20 or 1E8. Isreco 1 cells in suspension were incubated with anti-cytokeratin 8 antibodies (M20 and 1E8) for 45 min or with a corresponding antibody isotype (IgG). These cells were deposited on the Matrigel-covered filter of a modified Boyden chamber. After 17 h of invasion, the cells that crossed the filter were fixed, dyed and then quantified. The graphs above show normalized means of the absorbencies of the different wells of each sample. Significance: $*=p<0.05$, $=p<0.005$, $*=p<0.001$.

Figure 4:
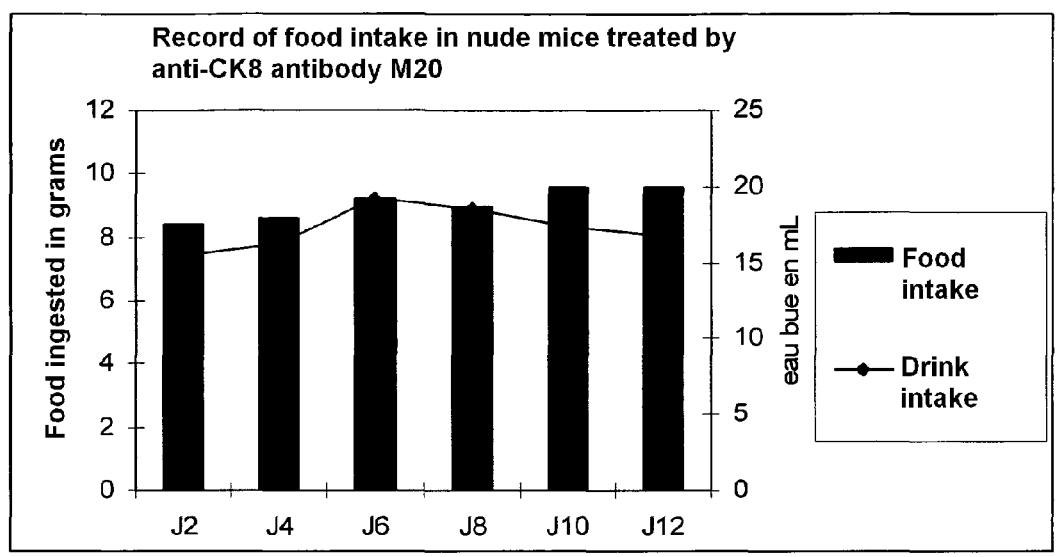

FIG. 4: Record of food intake on the nude mice treated with anti-CK8 antibody M20.

Figure 5:
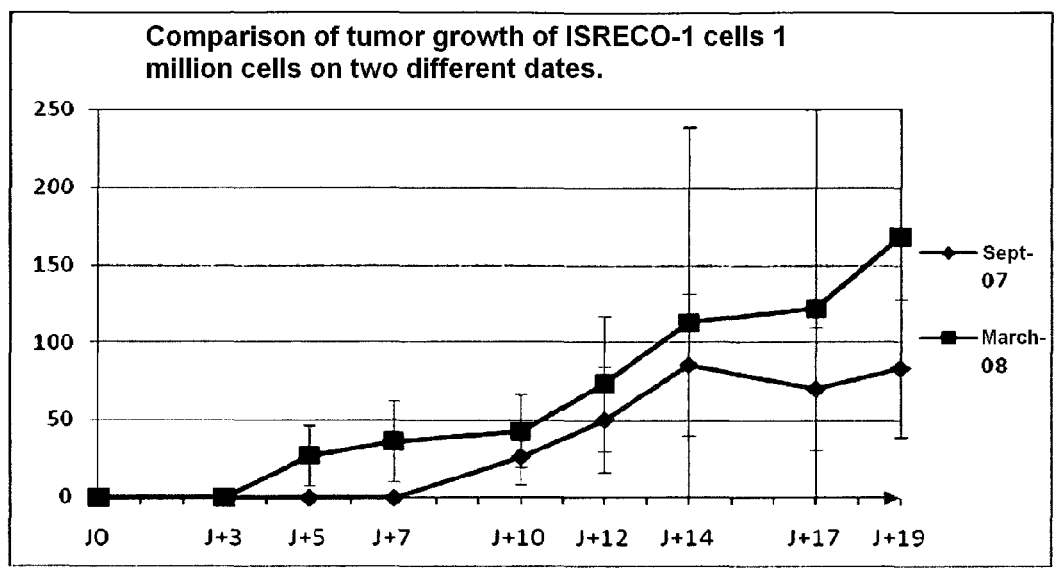

FIG. 5: Comparison of tumor growths of mice treated with ISRECO-1.

Figure 6:
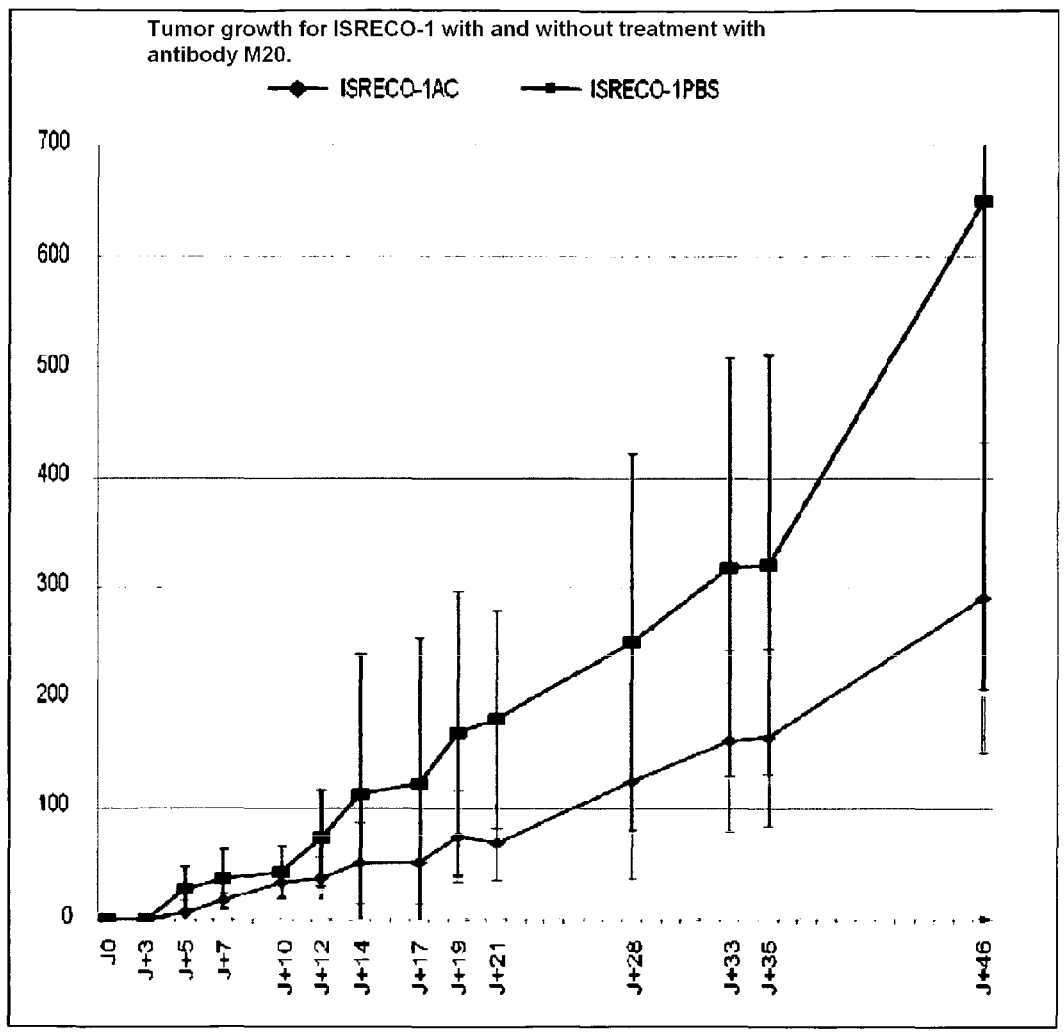

FIG. 6: Comparison of tumor growths of treated mice and controls.

EXAMPLES

Example 1

Cells, Culture Conditions and Treatment with Bombesin

See FIG. 1.

The human colon adenocarcinoma cell line Isreco 1 was provided by Prof. J-C. Saurin and Dr. J. Abello (Former Inserm Unit U45, Lyon—currently INSERM Unit U865). These adherent cells were cultured in DMEM (Dubelco's Modified Eagle's Medium, Gibco) containing 10% decomplemented fetal calf serum (FCS, Gibco) and 1% of a penicillin—streptomycin mixture (Gibco) kept in humid atmosphere at 37° C. and in the presence of 5% $CO_2$ For the bombesin treatment, the cells were plated in DMEM medium containing 0.1% bovine serum albumin (BSA) and 1% penicillin-streptomycin mixture. Forty-eight hours later, the culture medium was renewed and bombesin was added at a final concentration of 10 nM.

Example 2

Appearance of a Cleaved Form of CK8 and Characterization of the Cleavage

See FIG. 2.

The comparative analysis of IRESCO-1 cells not stimulated and stimulated by bombesin shows the very strong reduction in intensity of a band located at 53 kDa and the increase of intensity of a band located at 45 kDa. This observation has been confirmed by a 2PAGE analysis and by radioactive markers. These two proteins were identified by mass spectrometry: the 53 kDa form corresponds to the whole form of CK8 and the 45 kDa form corresponds to a cleaved form. The position of the cleavage site was assessed by western blot with antibodies specifically recognizing certain CK8 domains. This study allowed us to define the cleavage site as being located at the end of domain 2B at position 401 and more precisely around position 393 of CK8, i.e., in the last C-terminal third of the protein.

Example 3

Modulation of the Pro-Invasive Effect of BBS by Anti-CK8 Antibody

See FIG. 3.

Given that we have demonstrated the presence of CK8 on the external surface of the cells after stimulation by bombesin, the next step consists of determining if antibodies directed against CK8 can modulate the acquisition of invasiveness of Isreco 1 cells stimulated by BBS. For this, we reproduced the cell invasion protocol used to define the activity of BBS by using modified Boyden chambers (Saurin et al., Cancer Res, 2002). This protocol uses a 2 nM concentration of BBS enabling increasing invasion from 150 to 200%. A 10 nM concentration allowed obtaining greater effects, whose quantification is less precise. The cells were placed in modified Boyden chambers. They were subjected to or not subjected to the presence of BBS and placed over a Matrigel film. The activation of invasion induced the development of invasive processes of the Isreco 1 cells. In order to see this effect and the influence of antibodies, we measured the quantity of cells that crossed the filter after 17 h of incubation. The results are based on the means obtained from 7 to 11 independent wells per condition. We compared the influence of anti-CK8 M20 and anti-CK8 1E8 antibodies on the invasion of Isreco 1 cells through a membrane covered with Matrigel with regard to that of an antibody isotype. Antibody 1E8 recognizes the part that is cleaved following stimulation with bombesin. Note that performing invasion tests without antibody gives results similar to the use of an antibody isotype. The cells that invaded the matrix have been quantified and the means of the values were normalized by using the untreated sample containing the isotype antibody as a reference at 100%.

TABLE 1

Measuring the invasive capacity of Isreco 1 cells untreated or treated by bombesin in the presence of anti-cytokeratin 8 antibodies M20 or 1E8.

|  | BBS | Antibodies used | | | | |
|---|---|---|---|---|---|---|
|  |  | 1E8 | | | M20 | |
| Concentrations | 2 nM | 10 μg/mL | 25 μg/mL | 50 μg/mL | 10 μg/mL | 50 μg/mL |
| Isotype | – | 100 ± 8 | 100 ± 3 | 100 ± 3 | 100 ± 5 | 100 ± 9 |
| Anti-CK8 | – | 85 ± 7 | 88 ± 11 | 91 ± 10 | 95 ± 5 | 100 ± 6 |
| Isotype | + | 187 ± 12 | 161 ± 7 | 146 ± 6 | 150 ± 5 | 165 ± 6 |
| Anti-CK8 | + | 122 ± 11 | 124 ± 9 | 101 ± 13 | 141 ± 5 | 157 ± 6 |
| p value for the BBS effect |  | 0.0047 | 0.0015 | 0.0020 | 0.0015 | 0.0006 |
| p value for the antibody effect |  | 0.030 | 0.039 | 0.017 | 0.548 | 0.586 |

Table 1 shows the results for each concentration of antibody tested (10, 25 and 50 μg/mL for anti-CK8 M20 and 10 and 50 μg/mL for anti-CK8 1E8) with the corresponding standard deviations. Thus, we obtained a significant increase in the invasion of Isreco 1 cells in the presence of bombesin on all the operations with values comprised between 146% and 187% increase ($p<0.005$). The addition of the anti-CK8 antibody M20 induced a significant reduction of the quantity of invasive cells regardless of the concentration used ($p<0.05$). Conversely, the use of anti-CK8 antibodies hardly induced the inhibition of invasion activated by BBS treatment at all ($>0.5$). This result emphasizes the important functional role of extramembranous forms of CK8 (cleaved or uncleaved) in the aggressiveness of Isreco 1 cells induced by BBS.

Example 4

Safety Test for Anti-CK8 Antibody M20 on a Nude Mouse

The anti-CK8 monoclonal antibody called M20 is available commercially from SIGMA®. The goal of this study was to evaluate whether the inoculated antibody produced any physiological damage to the injected nude mouse.

a) Experimental protocol

Animal species

| Species: mouse | Strain: Swiss nude |
|---|---|
| Sex: female | Body mass: 20-25 grams |
| Origin: Charles River Laboratories France | |
| Domaine des Oncins-69592 L'Arbresle | |
| Health status: Specific Organism Pathogen Free | |

Treatment
Four injections in the tail vein of the treated mouse were done according to the following schedule:
Oct. 16, 2007 (D0)
Oct. 19, 2007 (D+5)
Oct. 23, 2007 (D+8)
Oct. 26, 2007 (D+12)
The dose administered was 0.1 mL or 100 μg M20 of antibody.
b) Results
Morbidity and Mortality:
The mouse did not show any sign of morbidity or mortality.
Food Intake:
The food and drink intake was 4.5 grams of food per day and 8.6 mL of water per day on average. The food intake record is shown in FIG. 4.
Animal Weight:
There was no notable variation in weight observed during this experiment.
Body mass of the nude mouse: 23 grams.
The injection of M20 anti-CK8 antibodies into a nude mouse had no effect on its health or behavior.

Example 5

Study of the Influence of the M20 AntiCK8 Antibody on the Growth of ISRECO-1 Tumors Grafted onto Nude Mice The purpose of this study was to evaluate the influence of antibody M20 on the growth of ISRECO-1 tumors grafted onto nude mice.

a) Experimental protocol:

Animal species:

| Species: mouse | Strain: Swiss nude |
|---|---|
| Sex: female | Body mass: 20-25 grams |
| Origin: Charles River Laboratories France | |
| Domaine des Oncins-69592 L'Arbresle | |
| Health status: Specific Organism Pathogen Free | |

TABLE 2

| ISRECO-1 AC "test" group | ISRECO-1 PBS "control" group |
|---|---|
| 1V | 1N |
| 2V | 2N |
| 3V | 3N |
| VN | NV |

Operating Protocol for ISRECO-1 Cells

Distribution of 12 Swiss Nude Mice into 2 Groups of 6 Mice

"Test" group: 2 Swiss nude mice intended to receive antibodies intravenously starting on D+3 after subcutaneous inoculation of ISRECO-1 cells on D0.

"Control" group: 6 Swiss nude mice intended to receive PBS intravenously starting on D+3 after subcutaneous inoculation of ISRECO-1 cells on D0.

The Tumor Suspension

The concentration of cells was 107 cells/mL. Subcutaneous injection of each of the 12 mice (106 ISRECO-1 cells in 100 μL/mouse).

The Antibodies to be Tested

On D+3, D+6, D+10 and D+13 the "test" group received 100 μg M20 anti-CK8 antibody intravenously. On the same dates, the "control" group received sterile PBS intravenously in the same volumes as the mice of the "test" group.

Tumor Measurement

The volume of the tumors was measured three times per week with the digital caliper according to the formula:

(length*width)2)/2

(Forest et al, Pathology Biology, 52:199-203, 2005).

The last measurement was done on the tumor extracted from the mouse after sacrifice.

b) Results

Comparison of Tumor Growth of Nude Mice from September 2007 and March 2008 Inoculated with ISRECO-1

6 mice were inoculated in each of the experiments with 106 ISRECO-1 cells

TABLE 3

Comparison of tumor growth (in mm3) with 106 ISRECO-1 cells (experiments of September 2007 and March 2008)

| Date | D 0 | D + 3 | D + 5 | D + 7 | D + 10 | D + 12 | D + 14 | D + 17 | D + 19 |
|---|---|---|---|---|---|---|---|---|---|
| September 2007 | 0 | 0 | 0 | 0 | 26.59 | 50.56 | 86.03 | 70.52 | 83.87 |
| March 2008 | 0 | 0 | 27.4 | 36.46 | 43.03 | 73.7 | 113.34 | 122.3 | 168.5 |
| standard deviation September 2007 | 0 | 0 | 0 | 0 | 18.07 | 34.11 | 45.69 | 39.5 | 44.7 |
| standard deviation March 2008 | 0 | 0 | 19.6 | 26.5 | 23.7 | 43.8 | 126.3 | 131.8 | 128.8 |

The comparison of tumor growth of mice treated with ISRECO-1 is shown in FIG. 5.

The tumor growth for ISRECO-1 injected in March 2008 began on D+3 while in September 2007 it began on D+7. On D+19, the mean tumor volume in March 2008 was 2 times greater than in September 2007.

Mice inoculated with ISRECO-1 cells: Comparison of tumor growth (volume in mm3) of mice treated with M20 antibody and untreated mice (PBS controls).

After inoculation of 106 cells, a group of 6 mice was treated with antibody M20 and a control group of 6 mice received the diluent alone (sterile PBS buffer, 0.14 M, neutral pH at D+3, D+6, D+10 and D+13).

TABLE 4

Comparison of tumor growth (mean volume in mm3) of mice treated with M20 antibody and untreated mice (PBS controls).

| Date | JO | D + 3 | D + 5 | D + 7 | D + 10 | D + 12 | D + 14 | D + 17 | D + 19 | D + 21 | D + 28 | D + 33 | D + 35 | D + 46 |
|---|---|---|---|---|---|---|---|---|---|---|---|---|---|---|
| ISRECO-1 AB | 0 | 0 | 6.3 | 16.9 | 33.2 | 36.9 | 50.6 | 51 | 74.6 | 68.9 | 124.25 | 161.24 | 164.27 | 291.12 |
| ISRECO-1 PBS | 0 | 0 | 27.4 | 36.5 | 42.5 | 73.7 | 113 | 122.3 | 168.5 | 181.1 | 250.91 | 318.58 | 320.65 | 649.87 |
| AB standard deviation | 0 | 0 | 9.892 | 7.48 | 13.09 | 18.78 | 36.7 | 36.96 | 41.36 | 33.77 | 88.54 | 81.55 | 80.03 | 140.5 |
| PBS standard deviation | 0 | 0 | 19.6 | 26.5 | 23.75 | 43.82 | 126 | 131.9 | 128.8 | 98.63 | 170.75 | 189.49 | 190.3 | 441.98 |

The tumor growth of mice treated with ISRECO-1 was inhibited from the first injection of antibody on D+3. On D+46, the mean size was 291.12 mm3 for the ISRECO-1 AB group, or 2.23 times less than the mean tumor volume for the untreated mice (649.87 mm3). The comparison of tumor growth of treated mice and controls is shown in FIG. 6.

The different values found for each of the mice are reported in Tables 5 and 6.

TABLE 5

Tumor growth in mice who received 106 ISRECO-1 cells treated with antibody M20 (volume in mm3).

| | Date | | | | | | |
|---|---|---|---|---|---|---|---|
| | D 0 | D + 3 | D + 5 | D + 7 | D + 10 | D + 12 | D + 14 | D + 17 |
| 1V | 0 | 0 | 0 | 12.2 | 15.56 | 18.92 | 20.6 | 21.02 |
| 2V | 0 | 0 | 0 | 12.2 | 34.91 | 33.69 | 39.8 | 43.42 |
| 3V | 0 | 0 | 0 | 12.2 | 35.91 | 24.99 | 27.5 | 25.23 |
| 4V | 0 | 0 | 16.38 | 16.8 | 46.21 | 60.86 | 111 | 110 |
| VR | 0 | 0 | 21.43 | 31.5 | 46.75 | 59.74 | 80.6 | 82.5 |
| VN | 0 | 0 | 0 | 16.4 | 19.7 | 23.06 | 24.5 | 23.89 |
| MEAN | 0 | 0 | 6.302 | 16.9 | 33.17 | 36.88 | 50.6 | 51.01 |
| standard deviation | 0 | 0 | 9.892 | 7.48 | 13.09 | 18.78 | 36.7 | 36.96 |

| | Date | | | | | |
|---|---|---|---|---|---|---|
| | D + 19 | D + 21 | D + 28 | D + 33 | D + 35 | D + 46 |
| 1V | 33.05 | 31.18 | 71.41 | 89.73 | 94.64 | 53.23 |
| 2V | 69.86 | 60.08 | 78.73 | 130.62 | 138.5 | 443.6 |
| 3V | 44.87 | 51.16 | 102.04 | 192.2 | 194.12 | 392.67 |
| 4V | 115.2 | 101.3 | 112.5 | 168.68 | 170.67 | 253.9 |
| VR | 135 | 119 | 302.09 | 303 | 303 | 360.85 |
| VN | 49.61 | 50.62 | 78.73 | 83.19 | 84.7 | 242.5 |
| MEAN | 74.6 | 68.88 | 124.25 | 161.237 | 164.27 | 291.13 |
| standard deviation | 41.36 | 33.78 | 88.538 | 81.551 | 80.027 | 140.55 |

TABLE 6

Tumor growth of mice that received 106 ISRECO-1 cells treated with sterile PBS (volume in mm3)

| | Date | | | | | | |
|---|---|---|---|---|---|---|---|
| | D 0 | D + 3 | D + 5 | D + 7 | D + 10 | D + 12 | D + 14 | D + 17 |
| 1N | 0 | 0 | 0 | 12.2 | 23.7 | 35.38 | 32 | 39.69 |
| 2N | 0 | 0 | 56.25 | 56.3 | 67.97 | 90.04 | 72.6 | 76.47 |
| 3N | 0 | 0 | 31.18 | 79.5 | 71.94 | 147.9 | 366 | 385.3 |
| 4N | 0 | 0 | 12.19 | 12.2 | 12.19 | 25.6 | 41.2 | 38.66 |
| NR | 0 | 0 | 37.26 | 29.5 | 36.82 | 67.5 | 106 | 113.5 |
| NV | 0 | 0 | 27.74 | 29.2 | 42.59 | 75.71 | 62.5 | 80.06 |
| MEAN | 0 | 0 | 27.44 | 36.5 | 42.54 | 73.7 | 113 | 122.3 |
| standard deviation | 0 | 0 | 19.63 | 26.5 | 23.75 | 43.82 | 126 | 131.9 |

| | Date | | | | | |
|---|---|---|---|---|---|---|
| | D + 19 | D + 21 | D + 28 | D + 33 | D + 35 | D + 46 |
| 1N | 37.26 | 58.82 | 58.82 | 74.44 | 76 | 109.8 |
| 2N | 115.3 | 147.8 | 167.13 | 261 | 261 | 800 |
| 3N | 373.5 | 320.6 | 451.2 | 599.04 | 600.3 | 1310 |
| 4N | 56.7 | 104.4 | 115.75 | 167.4 | 167.4 | 283.27 |
| NR | 259.9 | 265.7 | 459.42 | 416 | 418 | 907.5 |
| NV | 168.3 | 189 | 253.12 | 393.58 | 401.2 | 488.67 |
| MEAN | 168.5 | 181.1 | 250.91 | 318.577 | 320.65 | 649.87 |
| standard deviation | 128.8 | 98.62 | 170.75 | 189.499 | 190.3 | 441.98 |

The last measurement was taken after extraction of the tumor. The mouse epidermis was removed and the volume of the tumor was calculated as described previously.

For each mouse, time (in days) to reach different tumor volumes (50, 100, 150 and 200 mm3) is reported in Table 7.

TABLE 7

Time to reach 50, 100, 150 and 200 mm3 tumor volume by mouse.

| Mouse | Time (in days) for 50 mm$^3$ | Time (in days) for 100 mm$^3$ | Time (in days) for 150 mm$^3$ | Time (in days) for 180 mm$^3$ | Time (in days) for 200 mm$^3$ |
|---|---|---|---|---|---|
| Treated 1V | 26 | | | | |
| Treated 2V | 18 | 30 | 37 | 41 | 44 |
| Treated 3V | 20 | 28 | 30 | 32 | 36 |
| Treated 4V | 11 | 13 | 30 | 42 | 44 |
| Treated VR | 11 | 18 | 24 | 26 | 26 |
| Treated VN | 21 | 38 | 41 | 44 | 44 |
| Mean | 17.8 | 25.4 | 32.4 | 37 | 38.8 |
| standard deviation | 5.9 | 9.9 | 6.6 | 7.7 | 7.9 |
| Control 1N | 20 | 45 | | | |
| Control 2N | 4 | 18 | 22 | 32 | 32 |
| Control 3N | 6 | 11 | 13 | 13 | 13 |
| Control 4N | 18 | 20 | 32 | 37 | 37 |
| Control NR | 11 | 13 | 18 | 18 | 18 |
| Control NV | 11 | 13 | 18 | 21 | 24 |
| Mean | 11.6 | 20 | 20.6 | 24.2 | 24.8 |
| standard deviation | 6.6 | 10.9 | 7.1 | 9.9 | 9.8 |

The ISRECO-1 tumors treated with antibody M20 reached 50 mm3 in 18 days and grew to 200 mm3 in 38.8 days. In return, the untreated ISRECO-1 tumors had a delayed growth compared to the treated ones of 5 days to reach 100 mm3 then 14 days to reach 200 mm3.

To go from 100 to 200 mm3, the tumors of the treated mice had a doubling time of 13.4 days while for the control mice, the doubling time was much faster (4.8 days).

Anti CK8antibody M20 inhibits tumor growth in mice inoculated with ISRECO-1 cells.

REFERENCES

Doljak et al., Cancer Letters, 267:75-84, 2008 Erlandsson et al. (J. of Molecular Recognition, 16:157-163, 2003)

Forest et al., Pathology Biology, 52:199-203, 2005 Gires et al., Biochemical and Biophysical Research Communications, 328:1154-1162, 2005

Godfroid et al., Journal of Cell Science, 99:595-607 Hembrough et al., Journal of Cell Science, 108:1071-1082, 1995

Van Muijen, G. et al., Lab. Invest., 57:359, 1987 Waseem et al., Biochemistry, 43:1283-1295, 2004

PATENT REFERENCES

WO03/057168

The invention claimed is:

1. A method for treating colorectal cancer in a patient in need thereof comprising administering to said patient an effective amount of an antibody or antibody fragment, that specifically binds to the amino acids of position 338 to 367 of SEQ ID No. 1 of human CK8.

2. The method for treating colorectal cancer in a patient according to claim 1 wherein the antibody or antibody fragment specifically binds a fragment of at least 10 amino acids of the polypeptide having the sequence of the amino acids of position 338 to position 367 of SEQ ID No. 1 of human CK8.

3. The method for treating colorectal cancer in a patient according to claim 1 wherein said colorectal cancer is an invasive colorectal cancer.

4. The method according to claim 1 wherein said patient is selected with an identification method comprising the steps of:
   a) collecting a sample of colorectal cancer cells from said patient;
   b) detecting by immunohistochemistry or immunofluorescence the presence or the loss of the polypeptide resulting from the cleavage of the C-terminal part of CK8 in said cancers cells,
   c) classifying the colorectal cancer as invasive and/or metastatic when the C-terminal part of CK8 is cleaved.

5. The method according to claim 4 wherein said identification method comprises detecting the total or partial loss of the C terminal part of human CK8 on colorectal cancer cells with an antibody specifically binding a polypeptide having the sequence of the amino acids of position 402 to position 483 of SEQ ID No. 1 of human CK8, and an antibody binding the N-terminal part of human CK8 and further measuring the signal differential obtained to detect the total or partial loss of the C-terminal part of human CK8.

6. The method according to claim 5, wherein antibody binding the N-terminal part of human CK8 specifically binds a polypeptide having the sequence of the amino acids of position 1 to position 401 of SEQ ID No. 1 of human CK8.

7. The method according to claim 4, wherein the sample of colorectal cancer cells is a blood sample.

8. The method according to claim 4 wherein said identification method is performed with a diagnostic kit comprising an antibody specifically binding a polypeptide having the sequence of the amino acids of position 402 to position 483 of SEQ ID No. 1 of human CK8 and an antibody specifically binding a polypeptide having the sequence of the amino acids from position 1 to position 401 of SEQ ID No. 1 of human CK8.

9. The method according to claim 1 wherein said antibody is M20.

* * * * *